(12) United States Patent
Hurd

(10) Patent No.: US 12,708,691 B2
(45) Date of Patent: Aug. 18, 2026

(54) REFILLABLE VOLATILE COMPOSITION DISPENSER

(71) Applicant: The Procter & Gamble Company, Cincinnati, OH (US)

(72) Inventor: Eric Gunnar Hurd, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 658 days.

(21) Appl. No.: 18/119,309

(22) Filed: Mar. 9, 2023

(65) Prior Publication Data

US 2023/0285624 A1 Sep. 14, 2023

Related U.S. Application Data

(60) Provisional application No. 63/318,428, filed on Mar. 10, 2022.

(51) Int. Cl.
*A61L 9/12* (2006.01)
*A61L 9/04* (2006.01)
(Continued)

(52) U.S. Cl.
CPC ................. *A61L 9/12* (2013.01); *A61L 9/048* (2013.01); *B63B 23/16* (2013.01); *F42B 39/002* (2013.01);
(Continued)

(58) Field of Classification Search
CPC ........ A61L 9/12; A61L 9/012; A61L 2209/13; A61L 2209/131; A61L 2209/133; A61L 2209/15; F42B 39/002; Y10S 261/88
See application file for complete search history.

(56) References Cited

U.S. PATENT DOCUMENTS 4,372,490 A * 2/1983 Le Caire, Jr .............. A61L 9/12 220/4.24
4,762,275 A * 8/1988 Herbert ..................... A61L 9/12 239/45

(Continued)

FOREIGN PATENT DOCUMENTS

JP 2010280394 A 12/2010
JP 2020054583 A 4/2020
WO 2021237141 A1 11/2021

OTHER PUBLICATIONS

Search Report and Written Opinion for PCT/US2023/064001 dated Jul. 5, 2023, 11 pages.

*Primary Examiner* — Tuongminh N Pham
(74) *Attorney, Agent, or Firm* — Elizabeth A. Conklin; George H. Leal

(57) ABSTRACT

A volatile composition dispenser is provided. The volatile composition dispenser includes a housing having a base portion and a top portion rotatably and releasably connectable with the base portion about a longitudinal axis. The base and top portions each have a first surface and an opposing second surface. The housing includes a recessed track and a guide protrusion engageable with the recessed track. The recessed track has a track opening disposed at an open end of the recessed track and a track stop disposed at an opposite end of the recessed track. The recessed track is disposed on either the base portion or the top portion. When the recessed track is disposed on the base portion then the guide protrusion is disposed on the top portion. When the recessed track is disposed on the top portion then the guide protrusion is disposed on the base portion.

11 Claims, 16 Drawing Sheets

(51) Int. Cl.
*B63B 23/16* (2006.01)
*F42B 39/00* (2006.01)
*G21C 9/02* (2006.01)

(52) U.S. Cl.
CPC ........ *G21C 9/024* (2013.01); *A61L 2209/131* (2013.01); *A61L 2209/133* (2013.01); *A61L 2209/15* (2013.01)

(56) References Cited

U.S. PATENT DOCUMENTS 5,180,107 A 1/1993 Lindauer
2005/0285538 A1* 12/2005 Jaworski ................ A61L 9/037
422/123
2019/0168240 A1 6/2019 Beesley et al.
2020/0330637 A1 10/2020 Chang

* cited by examiner

REFILLABLE VOLATILE COMPOSITION DISPENSER

FIELD

The present invention is directed to a replenishable volatile composition dispenser, and, more particularly, is directed to a volatile composition dispenser having housing that is capable of receiving a volatile composition cartridge having a volatile composition.

BACKGROUND

Volatile compositions dispensers of various configurations are known. Some volatile composition dispensers are configured for one-time use and are then disposed of or recycled after the volatile composition is depleted. Volatile composition dispensers may be of a configuration that requires activation to release the volatile composition from the volatile composition dispenser for the first time. Such a volatile composition dispenser may only be activated one time, such that it would not be possible to refill or replenish the volatile composition and reactivate the volatile composition dispenser. As such, it would be beneficial to provide a volatile composition dispenser that are replenishable.

SUMMARY

"Combinations:"

A. A volatile composition dispenser comprising a housing, the housing comprising:
 - a housing comprising a base portion and a top portion that is rotatably and releasably connectable with the base portion about a longitudinal axis, wherein when the base portion and top portion are connected, an interior and exterior of the housing are defined, wherein the base portion comprises a first surface and a second surface opposing the first surface, and wherein the top portion comprises a first surface and a second surface opposing the first surface;
 - a recessed track;
 - a guide protrusion engageable with the recessed track, wherein the recessed track comprises a track opening disposed at an open end of the recessed track and a track stop disposed at an opposite end of the recessed track, wherein the recessed track is disposed on either the base portion or the top portion, and wherein when the recessed track is disposed on the base portion then the guide protrusion is disposed on the top portion, and wherein when the recessed track is disposed on the top portion then the guide protrusion is disposed on the base portion.

B. The volatile composition dispenser of Paragraph A, wherein the interior of the housing is configured to at least partially contain a volatile composition cartridge comprising a volatile composition.

C. The volatile composition dispenser of Paragraph A OR Paragraph B, wherein the base portion further comprises a mounting portion disposed on the second surface.

D. The volatile composition dispenser of any of Paragraphs A through C, wherein the base portion comprising a first surface and a second surface opposing the first surface, wherein the base portion further comprises an actuator extending from the first surface.

E. The volatile composition dispenser of any of Paragraphs A through D further comprising a cover that is removably connectable with the top portion.

F. The volatile composition dispenser of any of Paragraphs A through E, wherein the recessed track further comprises a restriction disposed adjacent to the track stop, wherein the track opening is configured to receive the guide protrusion.

G. The volatile composition dispenser of Paragraph F, wherein the recessed track further comprises an axially outermost point disposed adjacent to the track stop, wherein when the guide protrusion is positioned at the axially outermost point on the recessed track, the first surface of the base portion is closer to the second surface of the top portion than any other position of the guide protrusion on the recessed track.

H. The volatile composition dispenser of Paragraph G, wherein when the guide protrusion is positioned at the track stop, the first surface of the base portion and the second surface of the top portion are spaced axially farther apart than when the guide protrusion is positioned at the axially outermost point.

I. The volatile composition dispenser of any of Paragraphs A through H, wherein the top portion comprises an opening for exposing at least a portion of a volatile composition cartridge.

J. The volatile composition dispenser of any of Paragraphs A through I, wherein the housing comprises a plurality of air flow apertures.

K. The volatile composition dispenser of Paragraph J further comprising an air flow adjustment mechanism that is positionable in a first position and a second position, wherein in a first position the air flow adjustment mechanism covers at least a portion of the plurality of air flow apertures, and wherein in a second position the air flow adjustment mechanism exposes at least a portion of the plurality of air flow apertures to the exterior.

L. The volatile composition dispenser of any of Paragraphs A through K further comprising a volatile composition cartridge.

M. The volatile composition dispenser of any of Paragraphs A through L, wherein the interior is configured to receive a volatile composition cartridge comprising a membrane and a rupturable substrate.

N. The volatile composition dispenser of any of Paragraphs A through M, wherein the interior is configured to receive a volatile composition cartridge comprising a solid gel article.

O. The volatile composition dispenser of any of Paragraphs A through N, wherein the recessed track is disposed on the top portion and the guide protrusion is disposed on the base portion.

P. A method of refilling a volatile composition dispenser, the method comprising the steps of:
 - providing a volatile composition dispenser comprising a housing, the housing comprising:
   - a housing comprising a base portion and a top portion that is rotatably and releasably connectable with the base portion about a longitudinal axis, wherein when the base portion and top portion are connected, an interior and exterior of the housing are defined;
   - a recessed track;
   - a guide protrusion engageable with the recessed track, wherein the recessed track comprises a track opening disposed at an open end of the recessed track and a track stop disposed at an opposite end of the recessed track, wherein the recessed track is disposed on either the base portion or the top portion, and wherein when the recessed track is disposed on the base portion then the guide protrusion is disposed on the top portion, and wherein when the recessed track is disposed on the top portion then the guide protrusion is disposed on the base portion;

inserting a first volatile composition cartridge into the interior of the housing; aligning the guide protrusion with the track opening;

connecting the top portion and base portion by rotating one or both of the base portion and/or top portion about the longitudinal axis until the guide protrusion reaches the track stop;

separating the top portion and base portion by rotating one or both of the top portion and base portion about the longitudinal axis;

inserting a second volatile composition cartridge into the interior of the housing;

aligning the guide protrusion with the track opening; and connecting the top portion and base portion by rotating one or both of the base portion and/or top portion about the longitudinal axis until the guide protrusion reaches the track stop.

Q. The method of claim Paragraph P, wherein the volatile composition cartridge comprises a membrane and a rupturable substrate, wherein the recessed track comprises an axially outermost point, wherein the method further comprises the step of puncturing the rupturable substrate when the guide protrusion reaches the axially outermost point.

R. The method of Paragraph P or Paragraph Q, wherein the recessed track is disposed on the top portion and the guide protrusion is disposed on the base portion.

S. The method of any of Paragraphs P through R wherein the volatile composition dispenser further comprises a cover that is removably connectable with the top portion.

T. The method of any of Paragraphs P through S, wherein the housing comprises a plurality of air flow apertures.

DETAILED DESCRIPTION

Figure 1:
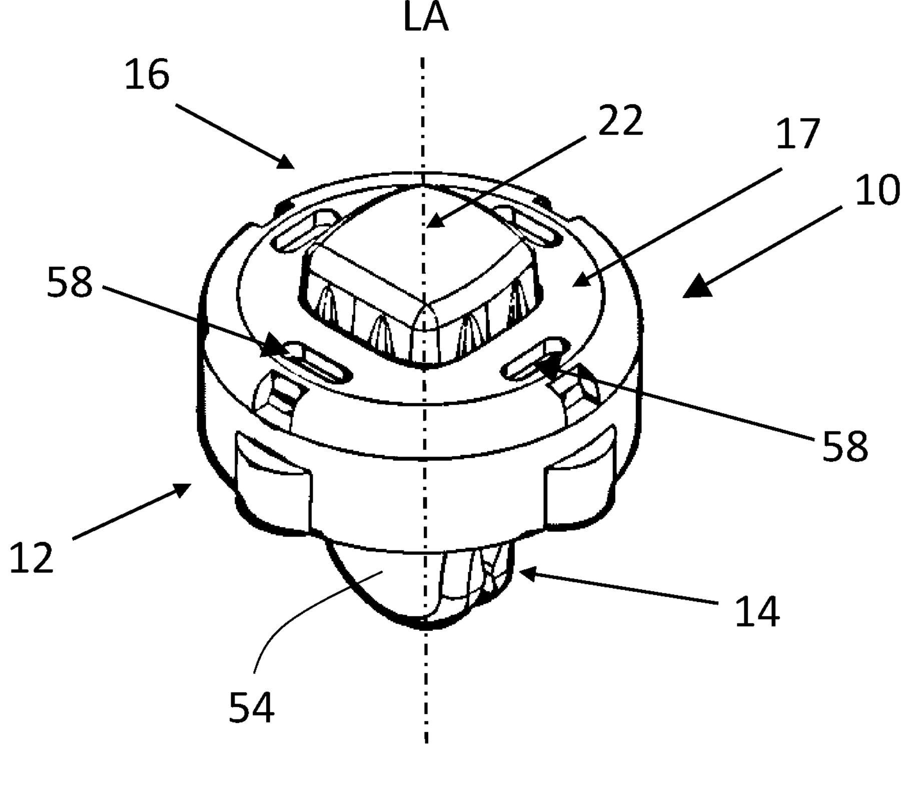
FIG. 1 is a top, perspective view of a volatile composition dispenser.

Various embodiments will now be described to provide an overall understanding of the principles of the structure, function, manufacture, and use of the apparatuses and methods disclosed herein. One or more examples of these embodiments are illustrated in the accompanying drawings. Those of ordinary skill in the art will understand that the apparatuses and methods specifically described herein and illustrated in the accompanying drawings are non-limiting example embodiments and that the scope of the various embodiments of the present disclosure is defined solely by the claims. The features illustrated or described in connection with one example embodiment may be combined with the features of other example embodiments. Such modifications and variations are intended to be included within the scope of the present disclosure.

A volatile composition dispenser can be used to dispense at least one volatile composition and/or other solution or composition, such as a perfume, a fragrance, and/or an insecticide, for example, to an area or atmosphere surrounding the volatile composition dispenser. The volatile composition can comprise a single chemical or a single material that is capable of entering the vapor phase under atmospheric conditions or, more commonly, the volatile composition can comprise a mixture of chemicals and/or materials that are capable of entering the vapor phase under atmospheric conditions.

The volatile composition can comprise, but is not limited to, a substance that can function as an air freshener, a deodorant, an odor neutralizing material, an odor blocking material, a malodor counteractant, an odor masking material, an aromatherapy material, an aromachology material, an insecticide, air and/or surface sanitizer, and/or a combination thereof. In other various embodiments, the volatile composition can comprise other various materials that can act in their vapor phase to modify, enhance, and/or treat an atmosphere or an area outside of the volatile composition dispenser.

The volatile composition dispenser can be configured to be used within an interior space or passenger compartment of a vehicle, for example, although the present invention is not limited to such use. While the volatile composition dispenser will be discussed herein with reference to use within a vehicle, those of skill in the art will understand that the dispenser can be configured for use in any environment, such as a home or an office, or can even be worn by a person, for example, and can be configured to dispense any suitable solution, chemical, material, and/or composition.

The volatile composition dispenser may be configured as non-energized volatile composition dispenser for the delivery of a volatile composition in a continuous manner "Non-energized" can mean that the apparatus is passive and does not require to be powered by a source of external energy. The volatile composition dispenser does not need to be powered by a source of heat, gas, or electrical current, and the volatile composition is generally not delivered by aerosol means.

The continuous emission of the at least one volatile composition can be of any suitable length, such as up to 20 days, 30 days, 40 days, 60 days, 90 days, shorter or longer periods, or any period between 10 to 90 days, for example. Of course, more or less volatile composition can be provided in the volatile composition dispenser to increase or decrease its useful life. Also, the volatile composition dispenser's useful life may be dependent on the conditions (i.e., temperature, pressure, moisture content, etc.) in which it operates.

When the volatile composition dispenser is configured for use in a car, the volatile composition dispenser may be positionable on a vent of an air handling system of a vehicle. The vent can comprise a plurality of louvers and a louver adjustment mechanism, for example. The volatile composition dispenser can be attached to the vent by engaging a mounting portion of the dispenser with the louvers, for example. In such an embodiment, air being forced or blown out of the vent by the air handling system can flow through the volatile composition dispenser to deploy any evaporated (i.e., vapor phase) volatile composition from the volatile composition dispenser to an interior space or passenger compartment of the vehicle. Such deployment of the volatile composition, as discussed above, can treat air within the passenger compartment or interior space of the vehicle, for example.

With reference to FIGS. 1-9, the volatile composition dispenser 10 includes a housing 12, defining a longitudinal axis LA. The housing 12 has at least a base portion 14 and a top portion 16 that is rotatably and releasably connectable with the base portion 14. When the base portion 14 and top portion 16 are connected, the base portion 14 and top portion 16 combine to define an interior 18 of the housing 12 and an exterior 20 of the housing 12. The interior 18 of the housing 12 is configured to at least partially surround and contain a volatile composition cartridge 22. The volatile composition cartridge 22 includes a volatile composition. The housing 12 may be reused when the volatile composition cartridge is depleted. When the volatile composition is depleted or nearly depleted from the volatile composition cartridge 22, the base portion 14 and top portion 16 can be separated and a new volatile composition cartridge 22 can be inserted into the housing 12. More specifically, the top portion and/or base portion may be rotatably and releasably connectable to each other about the longitudinal axis LA.

Figure 3:
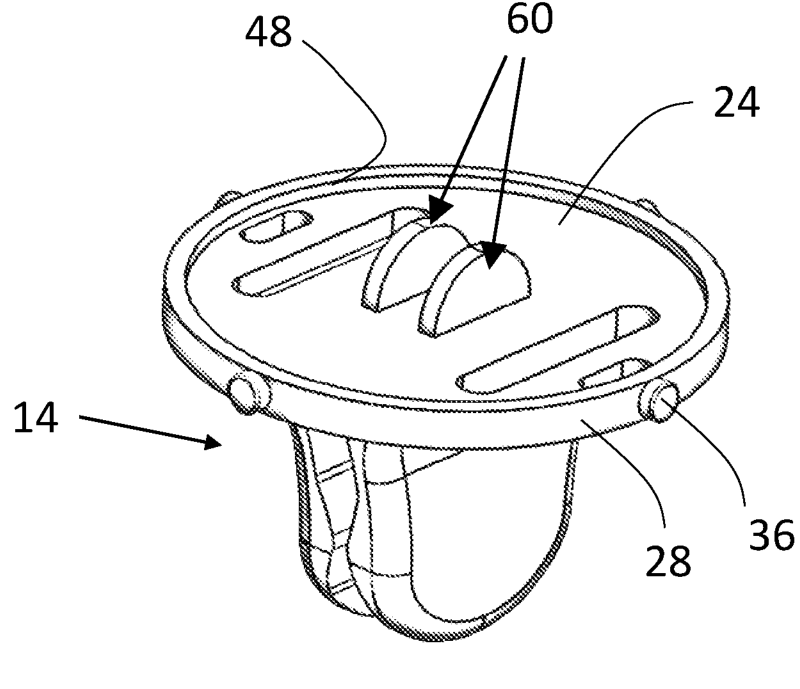
FIG. 3 is a top, perspective view of a base portion of a housing of a volatile composition dispenser.
Figure 4:
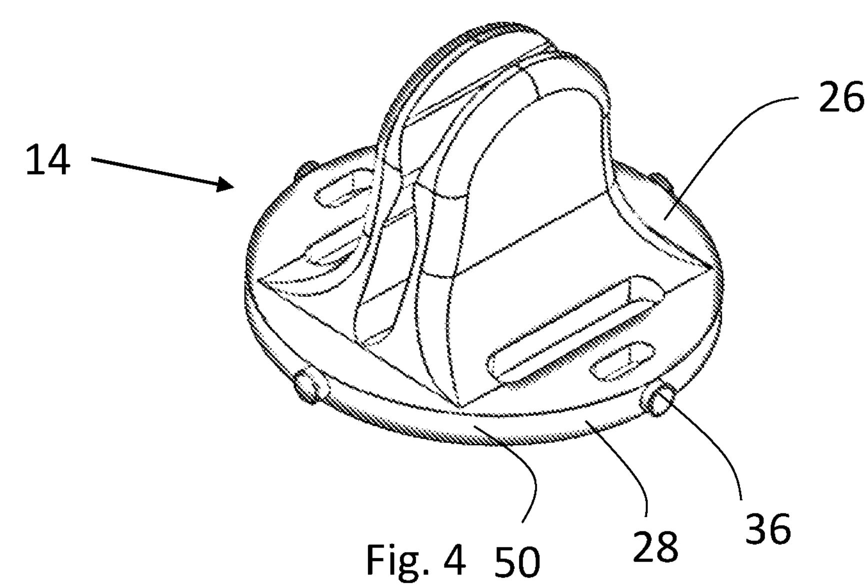
FIG. 4 is a bottom, perspective view of a base portion of a housing of a volatile composition dispenser.

With reference to FIGS. 3-4, the base portion 14 defines a first surface 24 and an opposing second surface 26. A sidewall 28 is disposed between the first and second surfaces 24 and 26 and circumscribes at least a portion of the first and second surfaces 24 and 26.

Figure 5:
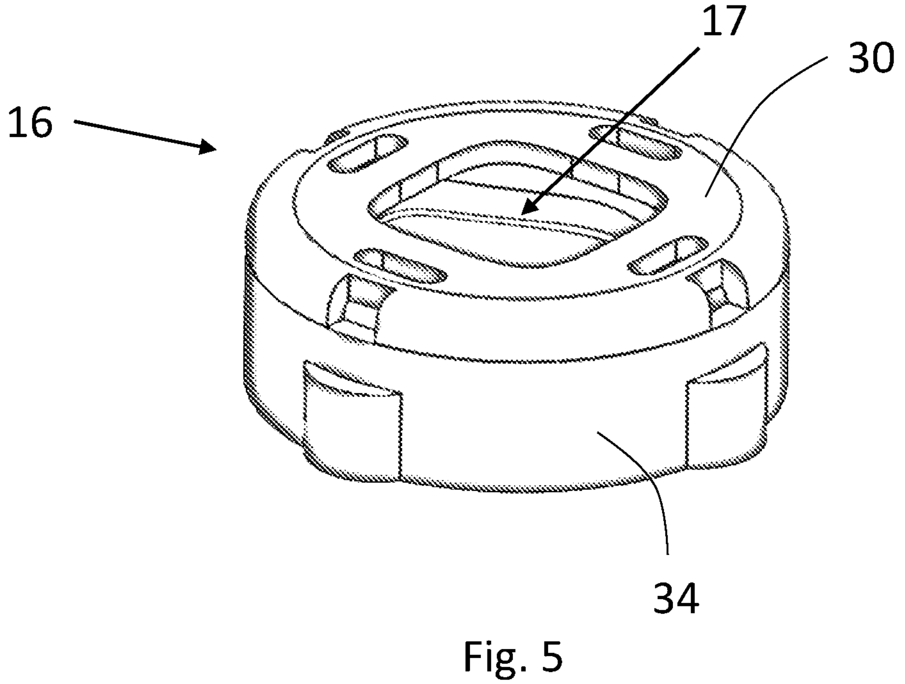
FIG. 5 is a top, perspective view of a top portion of a housing of a volatile composition dispenser.
Figure 6:
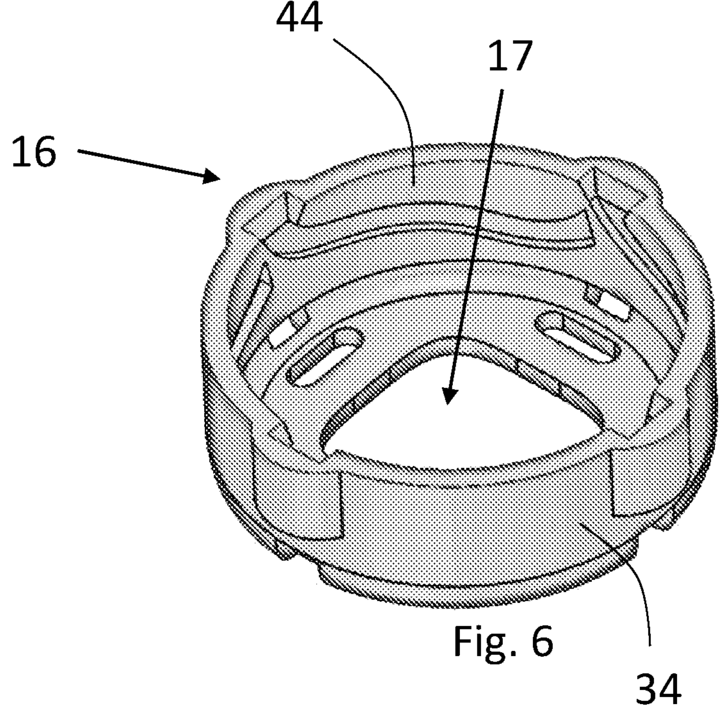
FIG. 6 is a bottom, perspective view of a top portion of a housing of a volatile composition dispenser.
Figure 7:
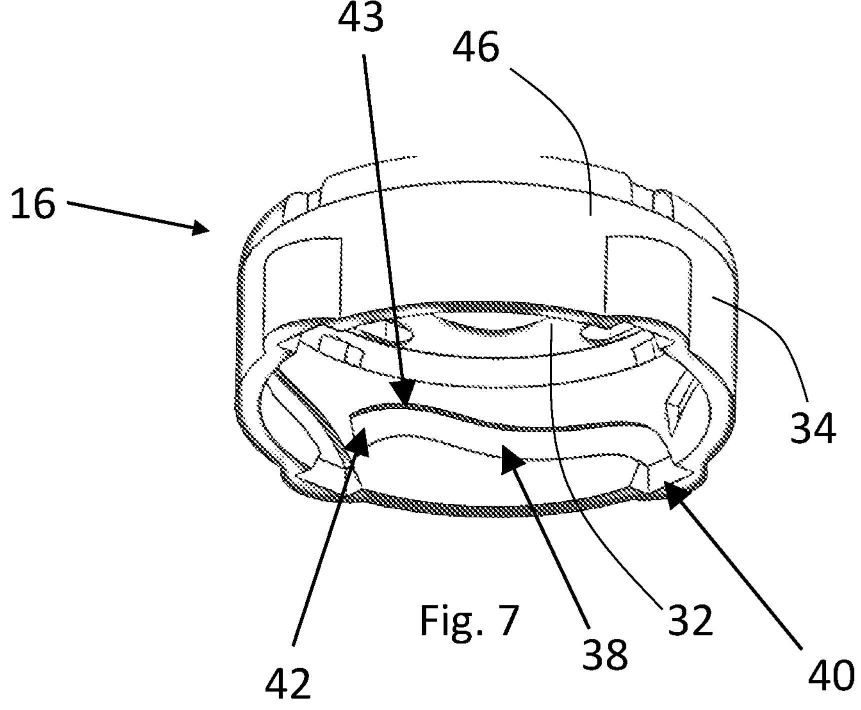
FIG. 7 is a bottom, perspective view of a top portion of a housing of a volatile composition dispenser.

With reference to FIGS. 5-7, the top portion 16 defines a first surface 30 and an opposing second surface 32. A sidewall 34 is disposed between the first and second surfaces 30 and 32 of the top portion 16 and circumscribes at least a portion of the first and second surfaces 30 and 32. The sidewall 34 defines an interior sidewall 44 and an exterior sidewall 46. The top portion 16 may include an opening 17 for exposing a portion of the volatile composition cartridge or to make the volatile composition cartridge viewable from the exterior.

The housing includes at least one guide protrusion(s) 36 and at least one recessed track(s) 38. The guide protrusion(s) 36 is either disposed on the base portion 14 or the top portion 16 of the housing. The recessed track(s) 38 is disposed on either the base portion 14 or the top portion 16. If the guide protrusion(s) 36 is disposed on the base portion 14, then the recessed track(s) 38 is disposed on the top portion 16. Likewise, if the guide protrusion(s) 36 is disposed on the top portion 16, then the recessed track(s) 38 is disposed on the base portion 14. The recessed track(s) 38 is configured to receive and guide a guide protrusion(s) 36 as the base portion 14 and top portion 16 are rotated relative to each other to either connect or disconnect the base portion 14 and top portion 16 from each other.

Figure 2:
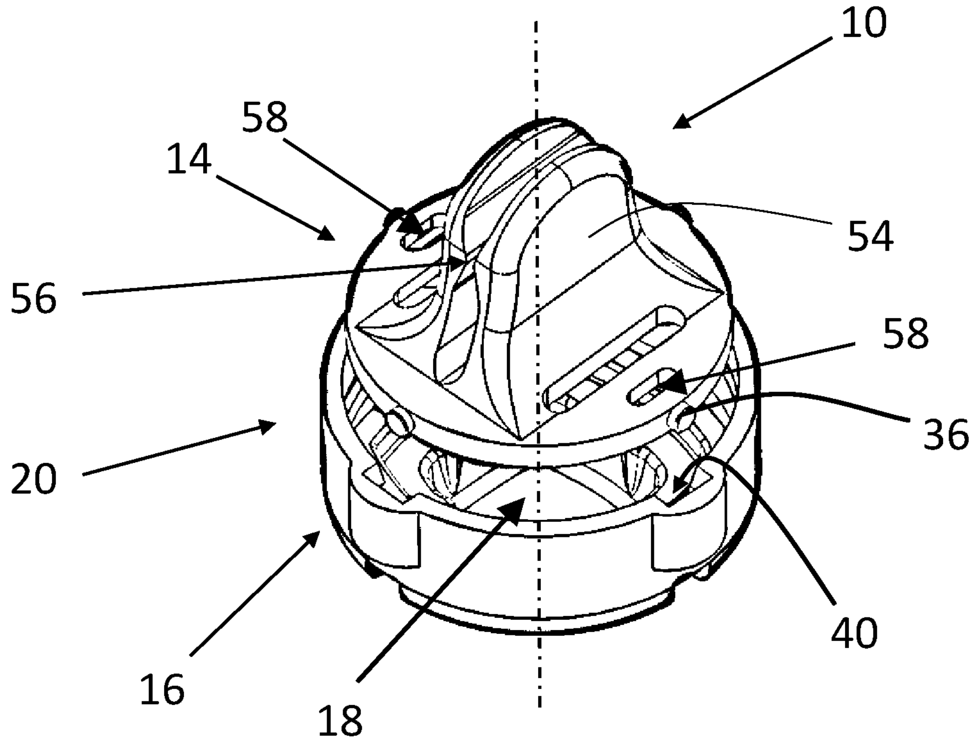
FIG. 2 is a bottom, perspective view of a volatile composition dispenser having a base portion disconnected from a top portion of a housing.

FIGS. 2-4 illustrate a non-limiting exemplary configuration where the at least one guide protrusion(s) 36 is disposed on the side wall 24 of the base portion 14. With reference to FIG. 7, the at least one recessed track(s) 38 is disposed on an interior sidewall 44 of the top portion 16.

Figures 8, 9:
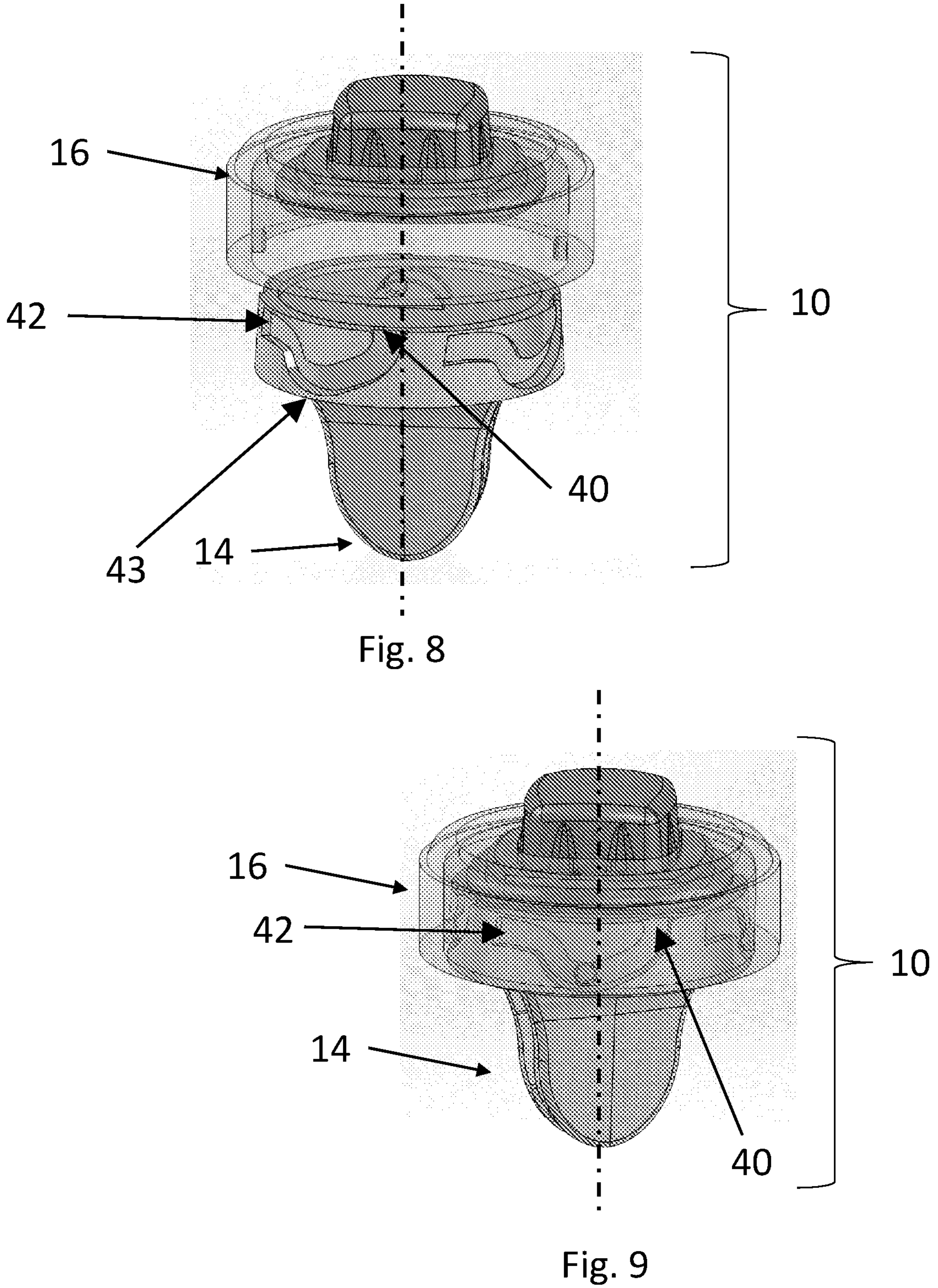
FIG. 8 is a side, perspective view of a volatile composition dispenser having a base portion disconnected from a top portion of a housing, illustrating details of a recessed track and guide protrusion. Some elements of the top portion are shown with transparency to view internal components not otherwise viewable from the exterior of the volatile composition dispenser.
FIG. 9 is a side, perspective view of a volatile composition dispenser having a base portion connected with a top portion of a housing, illustrating details of a recessed track and guide protrusion. Some elements of the top portion are shown with transparency to view internal components not otherwise viewable from the exterior of the volatile composition dispenser.

FIGS. 8-9 illustrate a non-limiting exemplary configuration where the sidewall 28 of the base portion 14 defines an interior sidewall 48 and an exterior sidewall 50. The at least one guide protrusion(s) may be disposed on the interior sidewall 44 of the top portion 16 and the recessed track(s) 38 may be disposed on the exterior sidewall 50 of the base portion 14.

With reference to FIGS. 6-9, the recessed track(s) 38 includes a track opening 40 and a track stop 42. In order to connect the base portion 14 and top portion 16 of the housing 12, a user can first align the guide protrusion(s) 36 with the track opening(s) 40 and then rotate one or both of the base portion 14 and top portion 16 relative to each other such that the guide protrusion(s) 36 moves circumferentially through the recessed track(s) 38. As the guide protrusion(s) 36 moves through the recessed track(s) 38, the base portion 14 and top portion 16 are brought closer together. The user rotates one or both of the first and second portions until the guide protrusion(s) 36 reaches the track stop(s) 42. Reaching the track stop 42 signals to the user that the first and second portions of the housing 12 are fully connected.

With reference to FIGS. 6-8, the recessed track(s) 38 may include an axially outermost point 43 disposed between the opening and the track stop. The axially outermost point 43 may be disposed adjacent to or at least relatively closer to the track stop 42 than the track opening 40. When the guide protrusion 36 is positioned at the axially outermost point 43, the first surface 24 of the base portion 14 is closer to the second surface 32 of the top portion 16 than any other position of the guide protrusion 36 on the recessed track 38. When the guide protrusion 36 is positioned at the track stop 42, the first surface 24 of the base portion 14 and the second surface 32 of the top portion 16 are spaced axially farther apart than when the guide protrusion 36 is positioned at the axially outermost point 43.

When the housing 12 comprises more than one recessed track 38 and guide protrusion 36, the recessed tracks have the substantially the same curvilinear shape such that the guide protrusions 36 travel through the recessed tracks 38 at the same time and in the same relative positions on the recessed tracks 38.

The guide protrusion(s) 36 may be various shapes. For example, the guide protrusion(s) 36 may be circular, oval, round, square, rectangular, triangular, and the like.

The recessed track(s) 38 may have a curvilinear shape. Recessed track(s) 38 can have a relatively uniform width that is sized to accommodate the guide protrusion(s) 36. The width the recessed track(s) 38 may be just slightly larger than the guide protrusion(s) 36.

Figure 10:
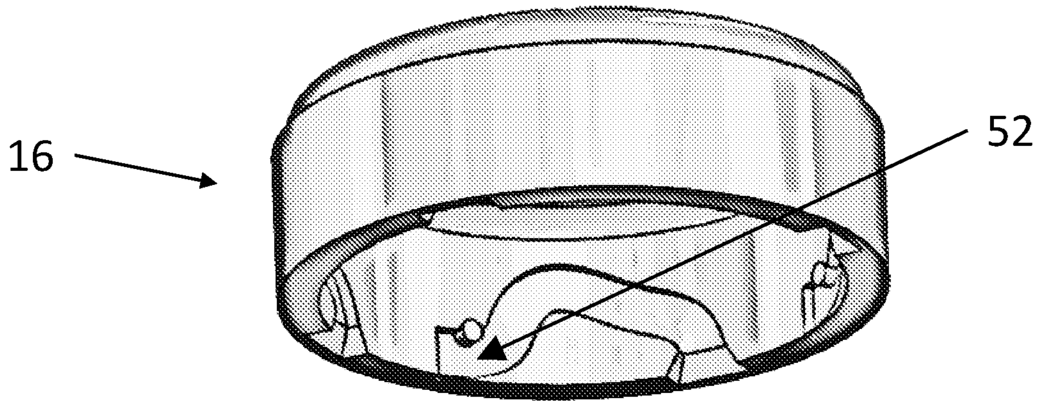
FIG. 10 is a bottom, perspective view of a top portion of a housing of a volatile composition dispenser having a restriction in a recessed track.
Figure 11:
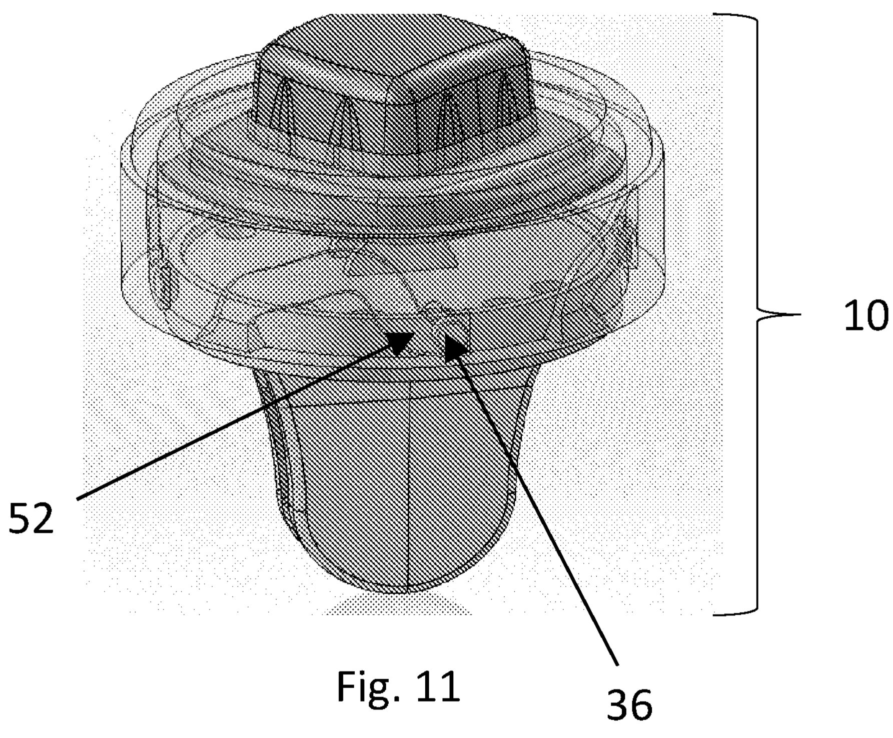
FIG. 11 is a side, perspective view of a volatile composition dispenser having a base portion connected with a top portion of a housing, illustrating details of a recessed track and guide protrusion. Some elements of the top portion are shown with transparency to view internal components not otherwise viewable from the exterior of the volatile composition dispenser.

As shown in FIGS. 10 and 11 for illustrative, non-limiting purposes only, the recessed track(s) 38 may include a restriction 52 that has a narrowed width adjacent to the track stop 42 to cause an interference fit for the guide protrusion(s) 36 at the track stop 42. The restriction 52 may help prevent the top portion 16 from prematurely separating from the base portion 14 during normal use of the dispensing device 10. The restriction 52 may also cause a "click" or similar sound when the user rotates the guide protrusion(s) 36 through the restriction 52. The restriction 52 should have a narrow enough width to restrict the top and base portions 16 and 14 from prematurely separating, but should not be too narrow of a width to prevent a user from being able to guide the guide protrusion 36 through the restriction on either assembly or disassembly of the housing 12. While the restriction 52 is shown on the top portion 16, it is to be appreciated that when the recessed track(s) 38 is disposed on the base portion 14, the recessed track(s) 38 may also include a restriction 52.

With reference to FIGS. 1 and 2, the volatile composition dispenser 10 may include a mounting portion 54. The mounting portion 54 may be connected with the base portion 14 of the housing 12. The mounting portion 54 may be joined with the second surface 26 of the base portion 14. The mounting portion 54 may be used to attach the volatile composition dispenser 10 to an object, such as a vent of air system of a vehicle, for example. As such, the mounting portion 54 can comprise one or more detents 56 configured to be engaged with portions of the object to which it attaches. Of course, the mounting portion 54 can also comprise any other suitable gripping or engaging features that would allow attachment of the volatile composition dispenser 10 to another object or the vent of an air system.

With reference to FIGS. 1 and 2, the base and/or top portions 14 and 16 of the housing 12 may include one or more air flow apertures 58. The air flow apertures 58 promote air flow in the interior of the housing 12. The air flow apertures 58 may promote air flow over the volatile composition cartridge to increase volatilization of the volatile composition from the volatile composition cartridge. Air may flow in the interior of the housing 12 through natural convection. Mounting the volatile composition dispenser 10 on a vent (i.e. a car vent or home HVAC vent) with the mounting portion can promote increased air flow through the interior of the housing 12.

The housing may include one or more actuators 60. With reference to FIG. 3, the actuator(s) 60 may be disposed on the base portion 14. As will be described in more detail below, the actuator(s) 60 may "activate" or release the volatile composition. The actuator 60 may be disposed on a surface of the base portion 14 opposite a mounting portion (when present). The actuator 60 may protrude from a first surface 24 of the base portion 14. The actuator may have various shapes. The actuator may have an arcuate or round shape, for example, More than one actuator may be used to cause a more uniform pressure distribution across the movable member of the rupture mechanism.

Figure 12:
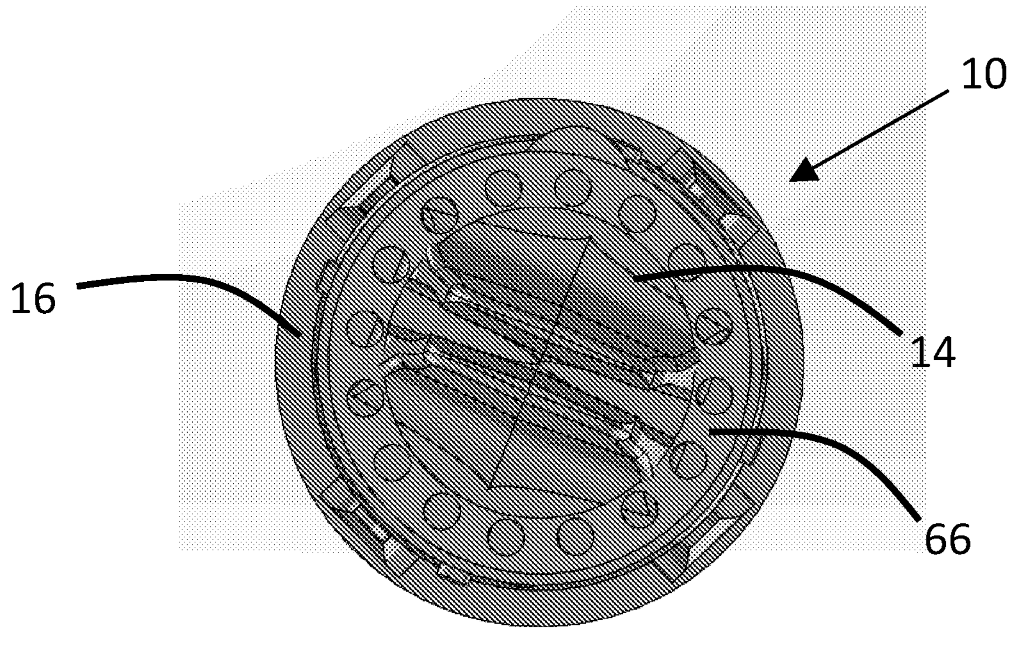
FIG. 12 is a bottom, plan view of a volatile composition dispenser having an air flow adjustment mechanism in a closed position.
Figure 13:
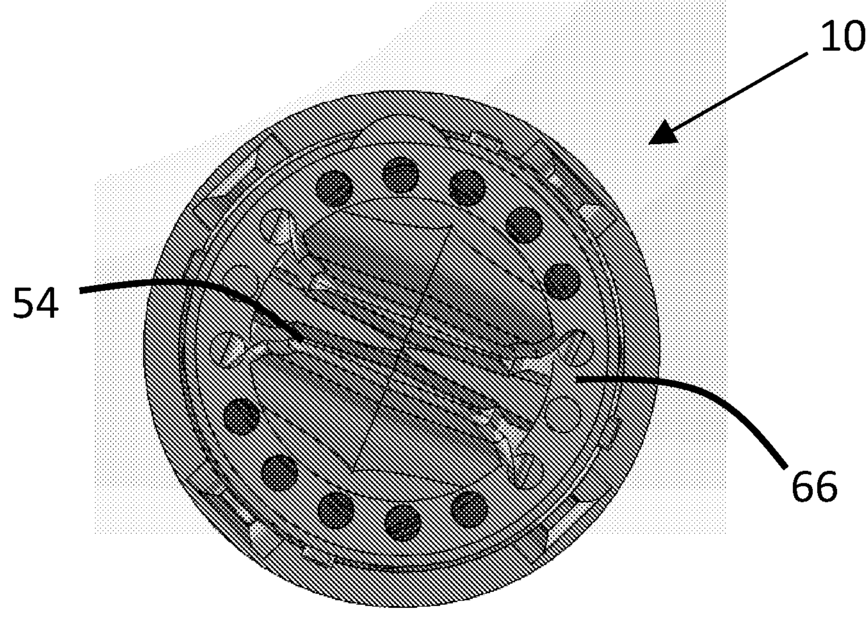
FIG. 13 is a bottom, plan view of a volatile composition dispenser having an air flow adjustment mechanism in an open position.

With reference to FIGS. 12 and 13, the volatile composition dispenser 10 may include an air flow adjustment mechanism 66 positioned over at least one air flow aperture. The air flow adjustment mechanism 66 may be connected with or formed with the first or second portions of the housing 12. The air flow adjustment mechanism 66 can be configured to move between at least a first position and a second position to at least partially cover or fully over at least one of the air flow apertures. An air flow adjustment mechanism 66 can be configured to move between a first position, such as shown in FIG. 12, at least partially covers all of the air flow apertures on the housing 12 to a second position, such as shown in FIG. 13, where it is free from covering all of the air flow apertures.

By providing an air flow adjustment mechanism, a user can adjust the air flow rate through the volatile composition dispenser 10 and thereby adjust the amount of evaporated volatile composition dispensed by the volatile composition dispenser 10 to an atmosphere surrounding the volatile composition dispenser 10. This feature gives the user the ability to essentially "customize" the volatile composition dispenser 10 to various personal preferences. If all of the air flow apertures are uncovered, more air can flow through the volatile composition dispenser 10 thereby providing more fragrance, malodor treatment etc. to an atmosphere surrounding the volatile composition dispenser 10. If at least some of the air flow apertures are covered, less air can flow through the dispenser thereby providing less fragrance, malodor treatments etc. to the atmosphere surrounding the volatile composition dispenser 10.

Figure 14:
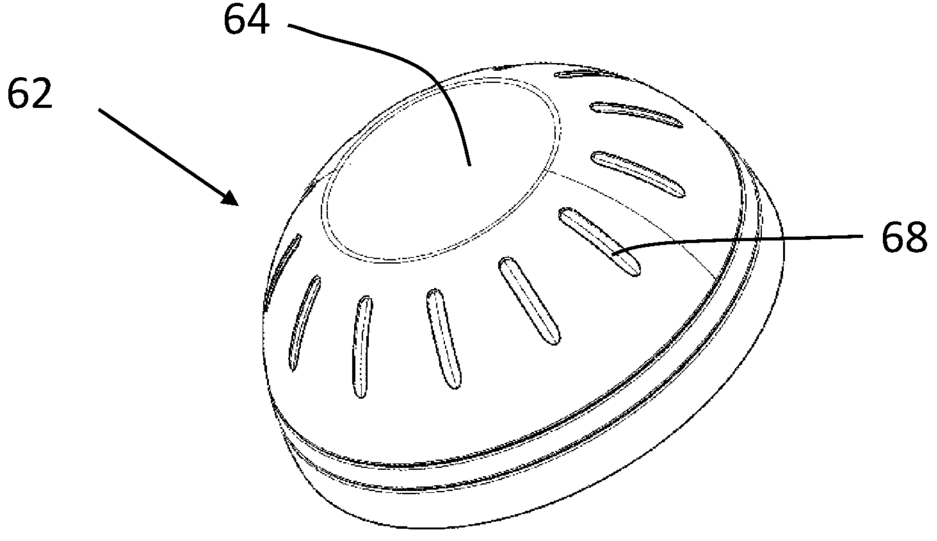
FIG. 14 is a perspective view of a cover for a volatile composition dispenser.
Figure 15:
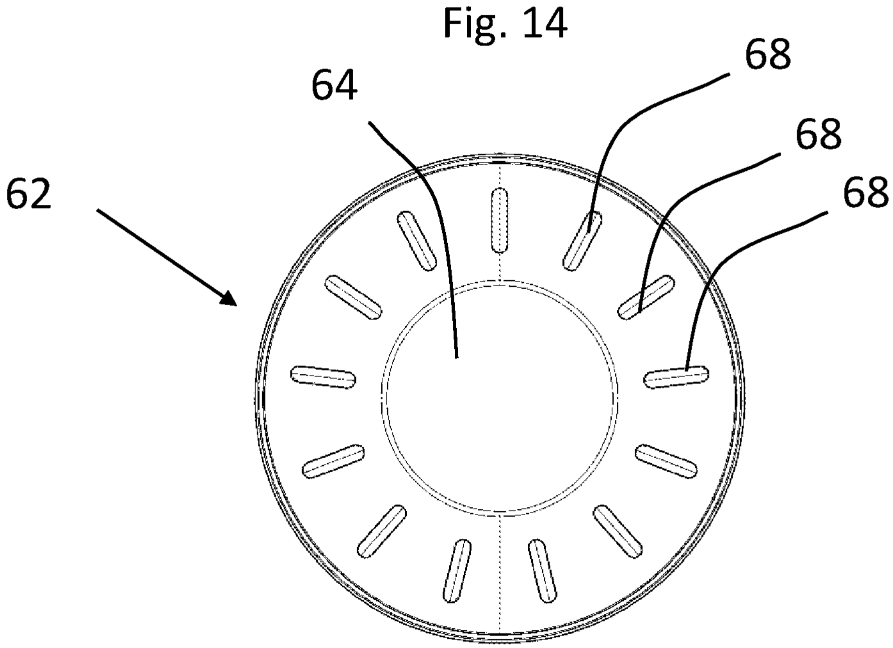
FIG. 15 is a top plan view of a cover for a volatile composition dispenser.
Figures 16, 17:
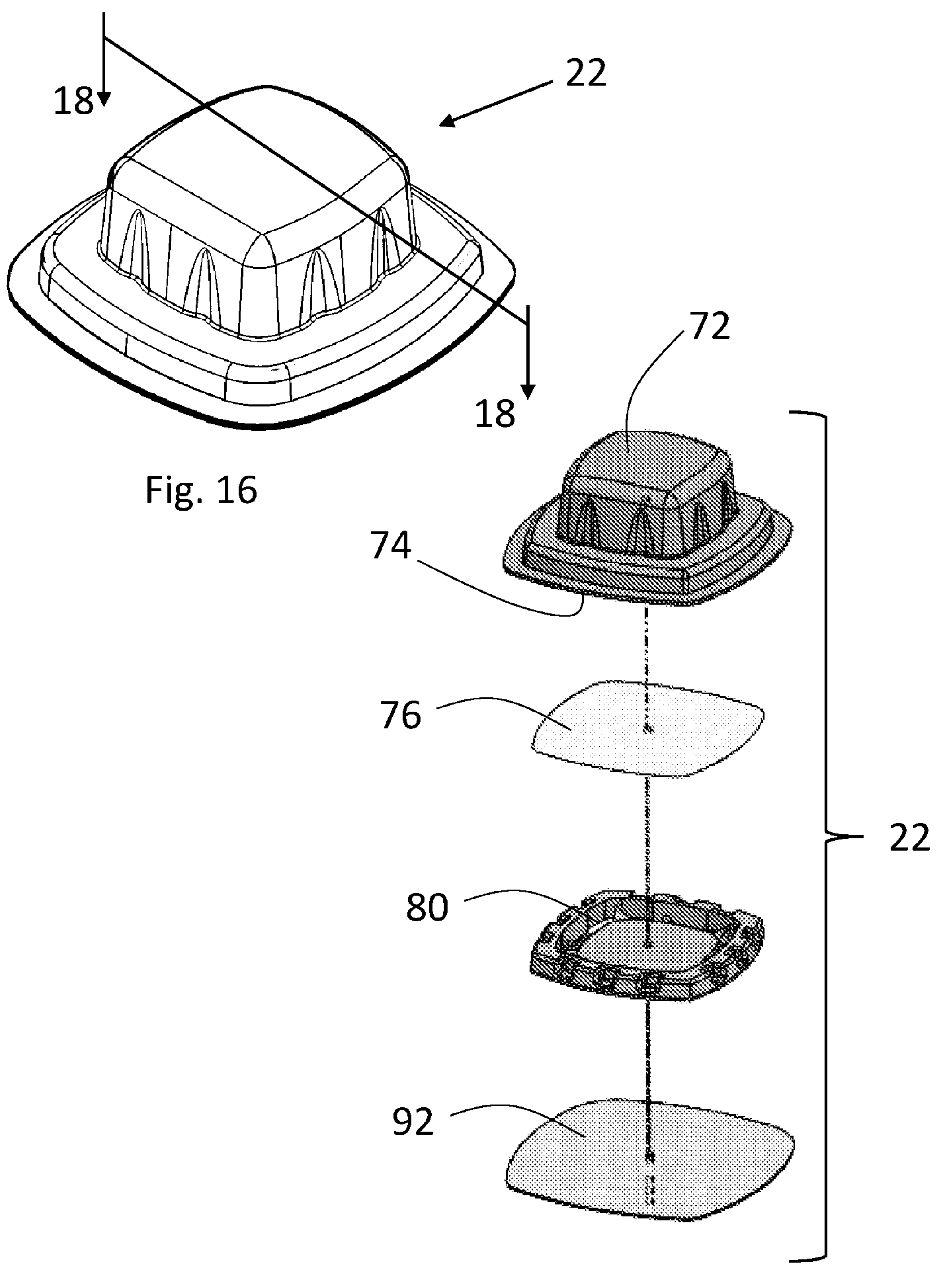
FIG. 16 is a perspective view of a volatile composition cartridge.
FIG. 17 is an exploded view of the volatile composition cartridge of FIG. 16.
Figure 18:
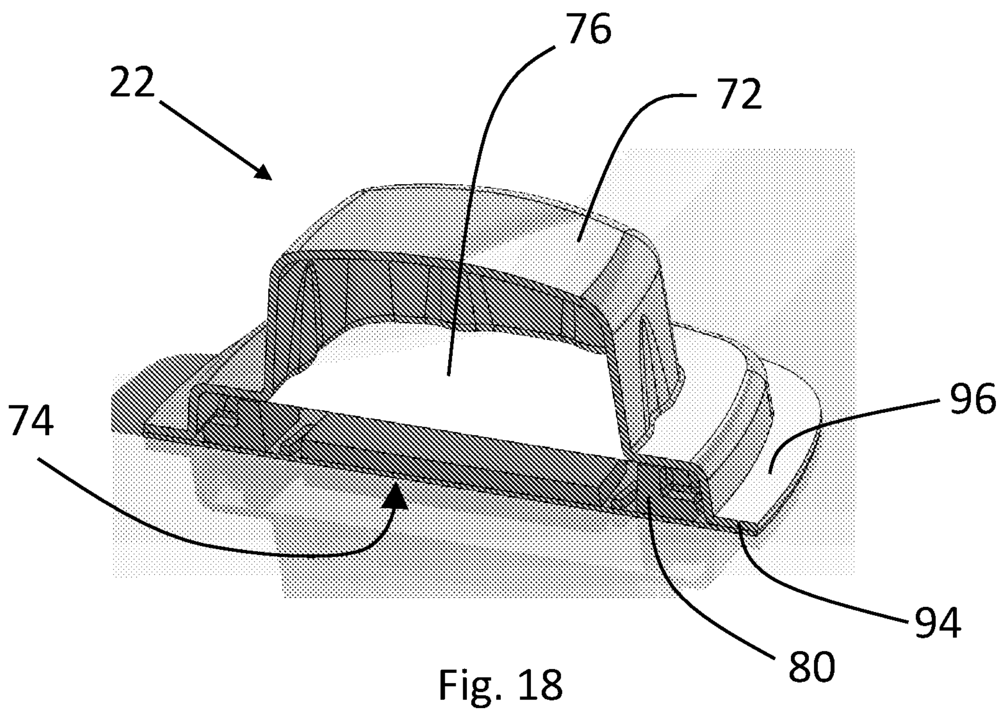
FIG. 18 is a sectional view of the volatile composition cartridge of FIG. 16.
Figure 19:
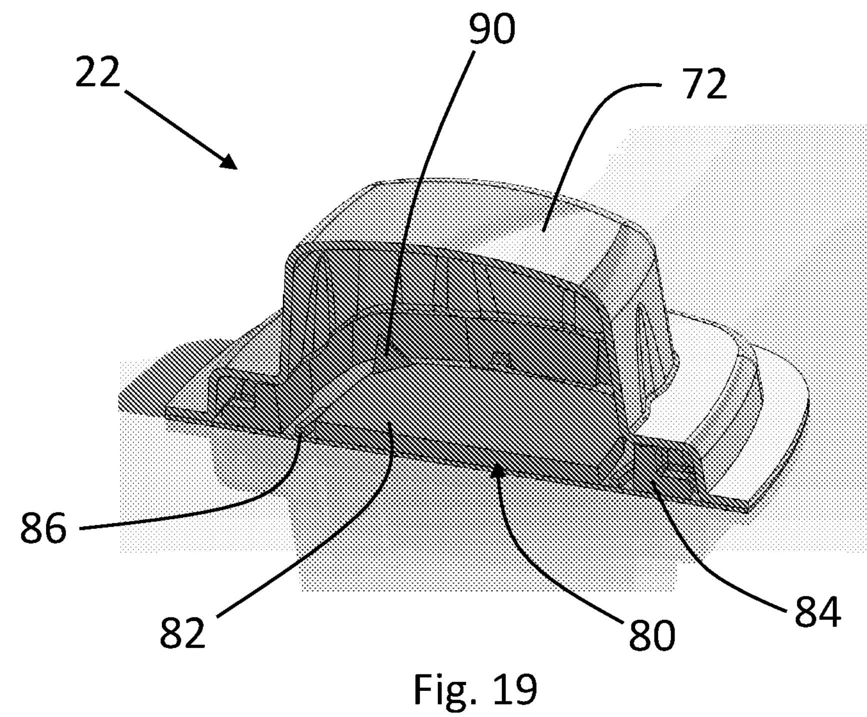
FIG. 19 is a sectional view of the volatile composition cartridge of FIG. 16 having a rupturable substrate removed to illustrate elements of a rupture mechanism.

With reference to FIGS. 14 and 15, the volatile composition dispenser 10 can include a cover 62 that is releasably connectable with the housing 12. The cover may be a decorative cover that is aesthetically pleasing to a user. Covers may be configured with various 3-dimensional designs. The cover may be interchangeable with the housing 12 such that the user is able to customize the volatile composition dispenser 10 to their individual aesthetic preference. The cover 62 may be connected with the top portion 14 and/or the base portion 12. The cover 62 may be configured to conceal all or a portion of the base portion and/or top portion 14. The cover 62 may include a window 64 configured for displaying the volatile composition cartridge 22. The window may be configured in various different shapes, including, for example, circle, oval, rectangle, square, and the like. The window 64 of the cover 62 may be the same or similar shape as the opening 17 in the top portion 16. The cover 64 may also include one or more air flow apertures 68. The cover 62 may be a separate component that is releasably connectable with the housing 12, or may be a separate component that is permanently attached with the top portion 16 of the housing 12, or the cover 62 may be integrally formed with the top portion 16 of the housing 12.

The volatile composition cartridge can be configured in a variety of ways. The volatile composition cartridge may contain a liquid volatile composition that is evaporated through a membrane. The volatile composition cartridge may also be in the form of a solid or semi-solid gel or wax.

With reference to FIGS. 16-22, the volatile composition cartridge 22 may include a container 72 having an orifice 74, within which a volatile composition 70 is stored. A rupturable substrate 76 is sealably attached to and covers the orifice 74 defining a reservoir to prevent the volatile composition 70 from being released until the volatile composition dispenser 10 is activated. The rupturable substrate 76 may be ruptured to release the volatile composition 70 by actuating a rupture mechanism 80 positioned adjacent to the rupturable substrate 76. The rupture mechanism 80 comprises a movable member 82 movably attached to an outer frame 84 by a resilient member 86. The resilient member 86 may be formed of one or more springs. One or more rupture elements 90 are arranged within the rupture mechanism 80 to puncture holes in the rupturable substrate 76. The rupture element 90 may come to a point 91 to assist in rupturing the rupturable substrate 76. The volatile composition cartridge 22 may comprise a membrane 92 disposed on the exterior of the volatile composition cartridge 22. The membrane 92 may be sealably attached to a flange 94 disposed at a periphery 96 of the container 72. The membrane 92 encloses the container 72, the volatile composition 70, the rupturable substrate 76, and the rupture mechanism 80. The membrane 92 may be configured to flex when a pressure or an actuation force is applied on the membrane 92.

With reference to FIGS. 18-22, the rupture elements 90 are spaced apart on the movable member 82. The position of the rupture elements 90 are configured to puncture at a hole at one side of the rupturable substrate 76 to allow air to enter the container 72 and another hole at an opposing side to drain the volatile composition from the container 72, which generates a pressure difference between the container interior and the container exterior. This pressure difference enables the volatile composition to be drained from one of the punctured holes disposed at the lower end of the rupturable substrate 76 as air enters the container 72 through the other punctured hole at the upper end of the rupturable substrate 76.

The internal components of the volatile composition cartridge 22 as shown in FIGS. 16-22 may be characterized as follows. For example, dimensions of the container 72 may be configured to hold about 1 ml to about 50 ml of a liquid volatile composition. Alternatively, the reservoir may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of a liquid volatile composition. Further, a shape of the container 72 may be configured to correspond to a shape of the opening 17 of the top portion. For example, the container 72 may define a substantially round, elliptical, or oval shape and its width to length ratio may be about 1:2 to 1:2.5.

The rupturable substrate 76 can be made of any material that ruptures with applied force, with or without the presence of an element to aid in such rupture. Because the rupturable substrate 76 is intended to contain a volatile material while in storage, it may be made from any barrier material that prevents evaporation of the volatile material prior to its intended use. Such materials may be impermeable to vapors and liquids. Suitable barrier materials for the rupturable substrate 76 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Suitable polymeric films include polyethylene terephtalate (PET) films, acrylonitrile copolymer barrier films such as those sold under the tradename Barex® by INOES, ethylene vinyl alcohol, and combinations thereof. It is also contemplated that coated barrier films may be utilized as a rupturable substrate 76. Such coated barrier films include metallized PET, metalized polypropylene, silica or alumina coated film may be used. Any barrier material, whether coated or uncoated, may be used alone and or in combination with other barrier materials.

The rupture mechanism 80 can be injection, compression, or pressure molded using a polyolefin, such as polyethylene or polypropylene; polyester; or other plastics known to be suitable for molding. The rupture mechanism 80 could also be made by thermoforming with a discrete cutting step to remove parts not wanted.

The membrane 92 may be a microporous membrane having an average pore size of about 0.01 to about 0.06 microns, alternatively from about 0.01 to about 0.05 microns, alternatively about 0.01 to about 0.04 microns, alternatively about 0.01 to about 0.03 microns, alternatively about 0.02 to about 0.04 microns, alternatively about 0.02 microns. Further, the membrane 9292 may be filled with any suitable filler and plasticizer known in the art. Fillers may include finely divided silica, clays, zeolites, carbonates, charcoals, and mixtures thereof. The microporous membrane 92 may be filled with about 50% to about 80%, by total weight, of silica, alternatively about 60% to about 80%, alternatively about 70% to about 80%, alternatively about 70% to about 75%. A thickness of the membrane 92 may be about 0.01 mm to about 1 mm, alternatively between about 0.1 mm to 0.4 mm, alternatively about 0.15 mm to about 0.35 mm, alternatively about 0.25 mm.

Still further, an evaporative surface area of the microporous membrane 92 may be about 2 cm2 to about 100 cm2, alternatively about 2 cm2 to about 25 cm2, alternatively about 10 cm2 to about 50 cm2, alternatively about 10 cm2 to about 45 cm2, alternatively about 10 cm2 to about 35 cm2, alternatively about 15 cm2 to about 40 cm2, alternatively about 15 cm2 to about 35 cm2, alternatively about 20 cm2 to about 35 cm2, alternatively about 30 cm2 to about 35 cm2, alternatively about 35 cm2. Accordingly, the rear frame 200 may be sized and shaped to fit the evaporative surface area of the membrane 92.

Suitable microporous membranes for the present invention include a microporous, ultra-high molecular weight polyethylene (UHMWPE) optionally filled with silica as described in U.S. Pat. No. 7,498,369. Such UHMWPE microporous membranes include Daramic™ V5, available from Daramic, Solupor®, available from DSM (Netherlands), and Teslin™, available from PPG Industries, and combinations thereof, and membranes available from Microporous LLC.

Figure 20:
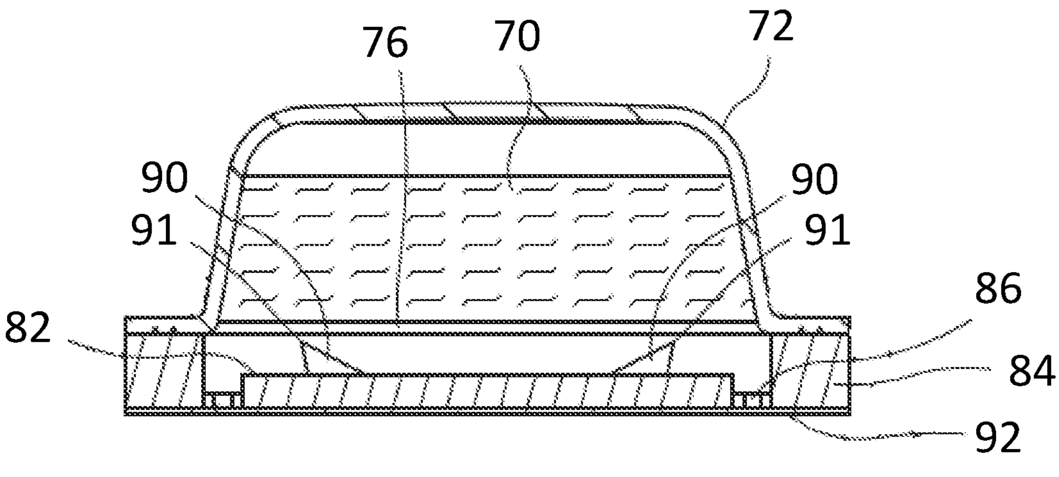
FIG. 20 is a sectional view of a volatile composition cartridge having a rupture mechanism in a deactuated, unpressurized state.
Figure 21:
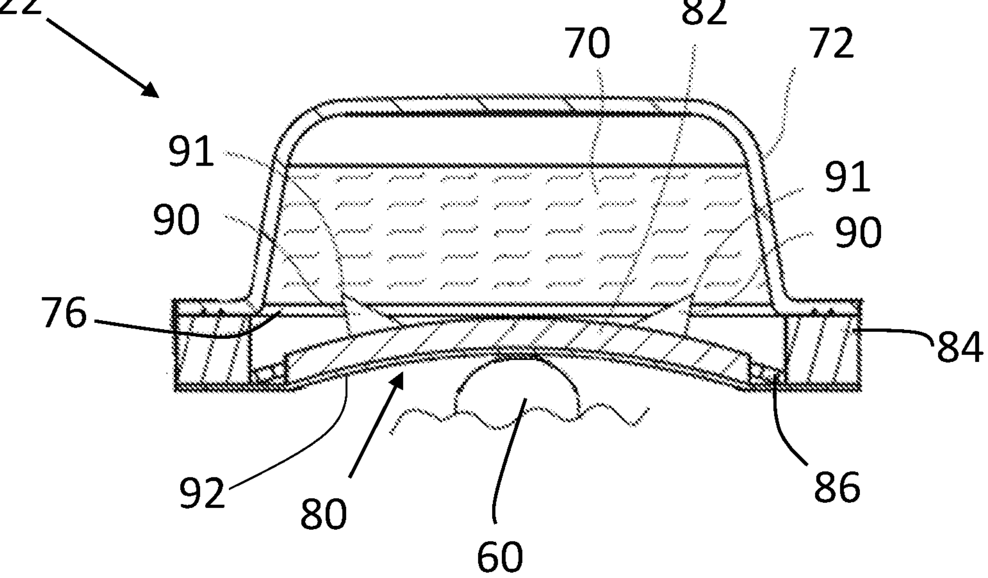
FIG. 21 is a sectional view of a volatile composition cartridge having a rupture mechanism in an actuated, pressurized state.
Figure 22:
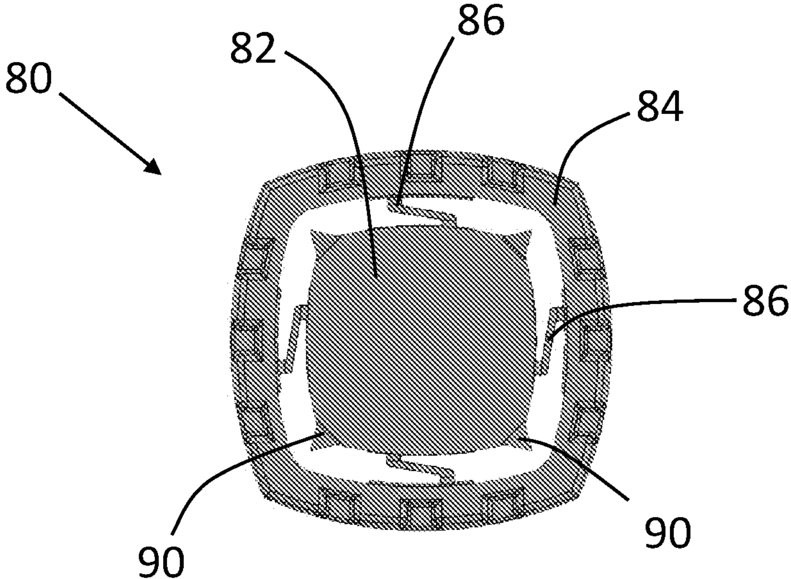
FIG. 22 is a top, plan view of a rupture mechanism of a volatile composition cartridge.
Figures 23, 24:
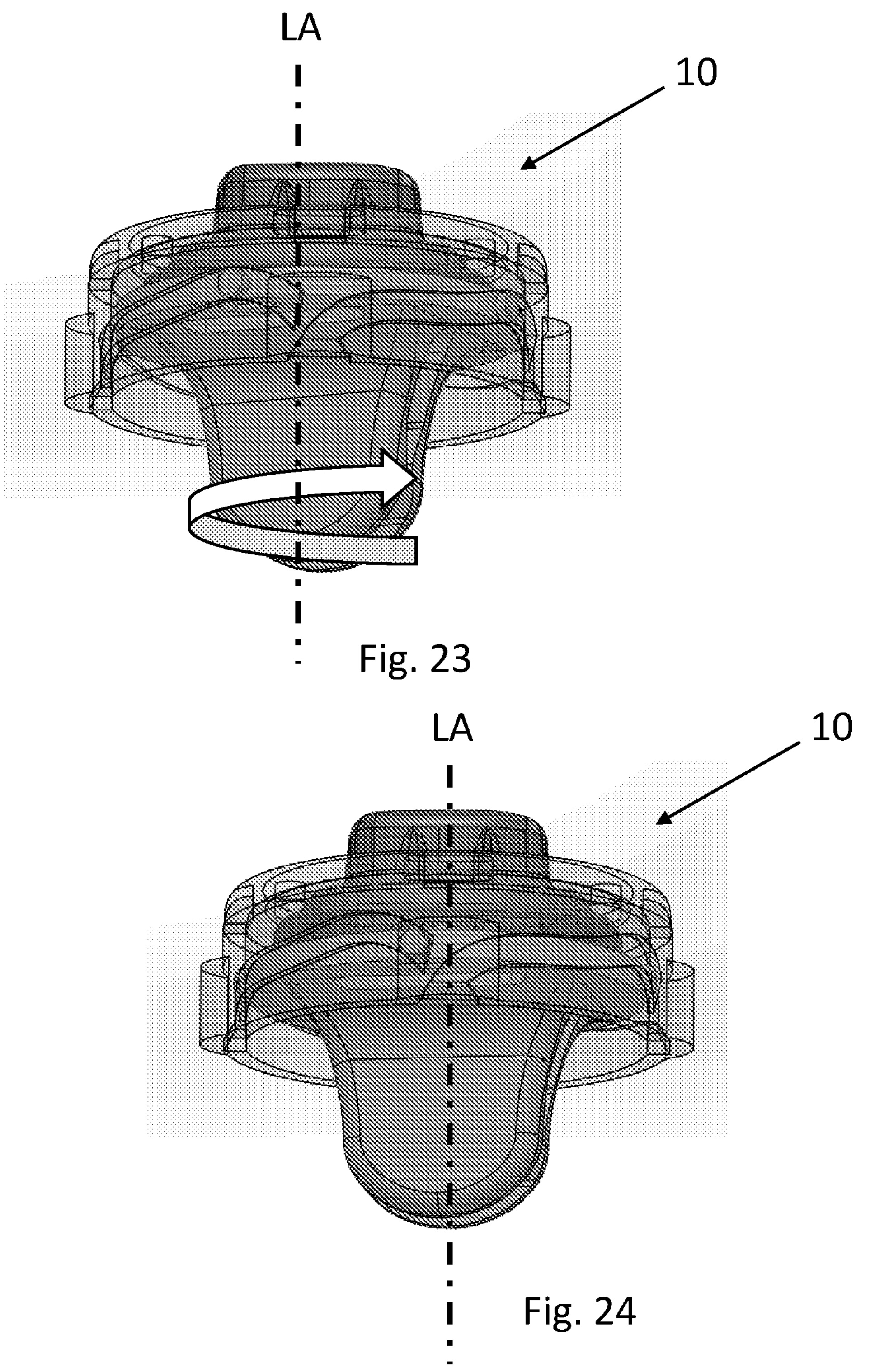
FIG. 23 is a side, perspective view of a volatile composition dispenser having a base portion connected with a top portion of a housing, illustrating a guide protrusion disposed at an axially outermost point of a recessed track as a user rotates and joins a top portion and a base portion of a housing. Some elements of the top portion are shown with transparency to view internal components not otherwise viewable from the exterior of the volatile composition dispenser.
FIG. 24 is a side, perspective view of a volatile composition dispenser having a base portion connected with a top portion of a housing, illustrating a guide protrusion disposed at track stop of a recessed track. Some elements of the top portion are shown with transparency to view internal components not otherwise viewable from the exterior of the volatile composition dispenser.

With reference to FIGS. 17, 20-21, and 23-25, when the volatile composition cartridge 22 that has a rupturable substrate 76, the actuator 60 on the base portion 14 can be used to rupture the rupturable substrate 76 and release the volatile composition 70 onto the membrane 92. The recessed track 38 is shaped such that as the guide protrusion 36 moves through the recessed track 38 as a user rotates the base portion 12 and/or top portion 14 together. When the guide protrusion 36 reaches the axially outer most point 43 on the recessed track 38, the actuator 60 is contacting and applying pressure to the membrane 92, which in turn applies pressure to the movable member 82 of the rupture mechanism 80. This exerted pressure on the movable member 82 causes the resilient members 86 to flex, bringing the rupture elements 90 into contact with the rupturable substrate and piercing the rupturable substrate 76 with the rupture elements 90, thereby forming holes in the rupturable substrate, such as shown in FIG. 21. Once holes are created in the rupturable substrate 76, the volatile composition is released for liquid absorption into the membrane for eventual release to the environment by evaporation over an extended period of time. Once this pressure on the rupturable substrate 76 results in the creation of holes, the user's continual rotation of the guide protrusion 36 through the recessed track 38 to the track stop 42 shifts the actuator 60 away from contacting and applying pressure to the membrane 92. Removing the pressure applied by the actuator 60 to the membrane 92 causes the resilient members 86 to flex back to the unpressurized state, such as shown in FIG. 20, which causes the rupture elements 90 to move away from the rupturable substrate 76. This retraction movement of the rupture elements 90 allows the holes to be unobstructed and allows for an easier flow of the volatile composition out of the receptacle and to the membrane 92.

Figure 25:
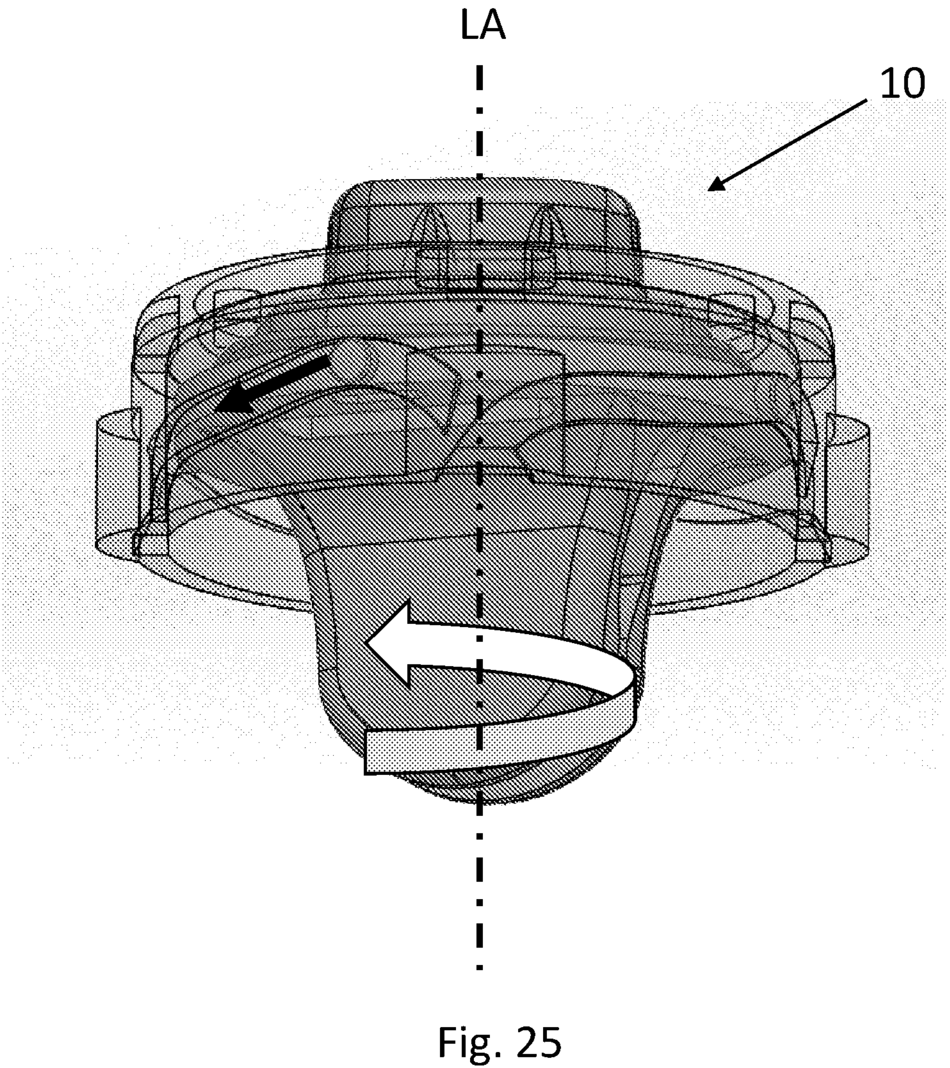
FIG. 25 is a side, perspective view of a volatile composition dispenser having a base portion connected with a top portion of a housing, illustrating a guide protrusion disposed at an axially outermost point of a recessed track as a user rotates and separates a top portion and a base portion of a housing. Some elements of the top portion are shown with transparency to view internal components not otherwise viewable from the exterior of the volatile composition dispenser.

When the volatile composition cartridge 22 is depleted of volatile composition, a user can separate the base portion 14 and the top portion 16 by rotating the base portion 14 and/or the top portion 16 away from each other such as shown in FIG. 25.

A volatile material or composition suitable for use in the volatile composition cartridge 22 for a volatile composition dispenser 10 may be configured to condition, modify, or otherwise change the atmosphere and may include compositions suitable for the purposes of providing fragrances, air fresheners, deodorizers, odor eliminators, malodor counteractants, insecticides, insect repellants, medicinal substances, disinfectants, sanitizers, mood enhancers, and aromatherapy aids. A list of the suitable volatile materials is shown in Table 2 below.

TABLE 2

| Purpose | Volatile Material |
| --- | --- |
| Providing fragrances | Perfume oil, volatile essential oils, volatile organic compound, synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. Suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like. |
| Neutralize malodors | Suitable malodor compositions include reactive aldehydes and ionones |

The composition may be formulated such that the composition comprises a volatile material mixture comprising about 10% to about 100%, by total weight, of volatile materials that each having a VP at 25° C. of less than about 0.01 torr; alternatively about 40% to about 100%, by total weight, of volatile materials each having a VP at 25° C. of less than about 0.1 torr; alternatively about 50% to about 100%, by total weight, of volatile materials each having a VP at 25° C. of less than about 0.1 torr; alternatively about 90% to about 100%, by total weight, of volatile materials each having a VP at 25° C. of less than about 0.3 torr. The volatile material mixture may include 0% to about 15%, by total weight, of volatile materials each having a VP at 25° C. of about 0.004 torr to about 0.035 torr; and 0% to about 25%, by total weight, of volatile materials each having a VP at 25° C. of about 0.1 torr to about 0.325 torr; and about 65% to about 100%, by total weight, of volatile materials each having a VP at 25° C. of about 0.035 torr to about 0.1 torr. One source for obtaining the saturation vapor pressure of a volatile material is EPI Suite™, version 4.0, available from U.S. Environmental Protection Agency.

Figure 26:
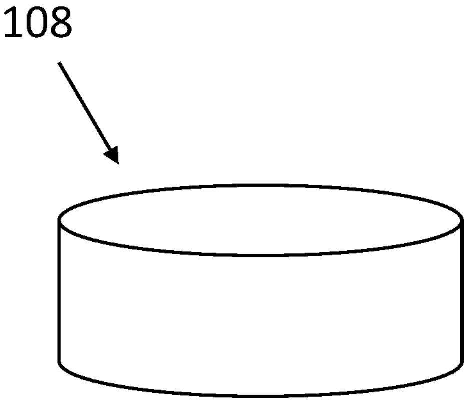
FIG. 26 is a side, perspective view of a volatile composition cartridge in the form of a solid gel article.

With reference to FIG. 26, the volatile composition cartridge 22 may be in the form of a solid gel article 108. The solid article may be molded with a moldable material such as any one of the gel compositions described hereinafter.

The gel composition can be a chemically cross-linked polyol or derivative thereof. Suitable polyols or derivatives thereof can be selected from the group consisting of: polyol, polyester polyol, polyglycerol and mixtures thereof. Polyols, polyester polyols and polyglycerols comprise multiple hydroxyl groups, and are suitable for forming gels having a compact network. In addition, the resultant gel has greater affinity for hydrophobic materials which are less strongly hydrophobic.

Suitable polyols or derivatives thereof can have a molecular weight of from 60 Da to 10000 Da, preferably from 150 Da to 3000 Da, even more preferably from 500 Da to 2000 Da, even more preferably 600 Da to 1300 Da. Longer polyols and derivatives thereof, result in greater flexibility of the gel.

Suitable polyols and derivatives thereof do not comprise terminal hydroxyl groups. Secondary alcohols are particularly suitable. Primary alcohols, having terminal hydroxyl groups, typically result in more linear chains and a more compact network. A combination of primary and secondary alcohols are preferred, since they result in a more desired correlation length.

An average correlation length of less than 8 nm as measured using Small Angle X-Ray Scattering (SAXS) is preferred. However, the gel compositions, described herein, can be formulated to have any desired correlation length.

A gel with more optimal pore size is achieved when secondary alcohols are used. Lightly branched polyols and derivatives thereof, such as poly(diethyleneglycol adipates) result in more flexible gels. Preferred polyols and derivatives thereof have at least 2 hydroxyl groups per molecule, more preferably at least 3 hydroxyl groups per molecule.

A polyol is a compound containing multiple hydroxyl groups. Diol polyols, having two hydroxyl-functional groups, result after cross-linking in linear polymers or more open networks having large pore size. In contrast, hydroxyl-functional monomers with functionality larger than two form more compact gels with smaller pore sizes. Suitable polyols include: ethylene glycol, propylene glycol, 1,4-butanediol, 1,6-hexanediol, pentaerythritol, 1,2,6-hexanetriol, 4,6-di-tert-butylbenzene-1,2,3-triol, propanetriol (glycerol), 1,2,5-hexanetriol, 1,2,4-cyclohexanetriol, 2,5-dimethylhexane-1,2,6-triol, 3-hydroxymethylpentane-1,2,5-triol, 1,3,6-hexanetriol, 1,1,5,5-pentanetetraol, 1,2,5,6-hexanetetraol, 1,2,3,4,5,6-hexanehexol (sorbitol) and mixtures thereof.

Polyester polyols are hydroxyl-containing esters. Suitable polyester polyols can be selected from the group consisting of: aliphatic polyester polyols, aromatic polyester polyols, organic oil based polyester polyols, and mixtures thereof. Organic oil based polyester polyols are preferred. Preferred organic oils are vegetable oils since they typically comprise high levels of unsaturation (C═C bonds) and naturally comprise hydroxyl groups. Suitable polyester polyols include: hexanoic acid, 4-hydroxy-, 1,1',1"-(1,2,3-propanetriyl) ester; pentanoic acid, 5-amino-4-hydroxy-, 1,1',1"-(1,2,3-propanetriyl) ester; Polycaprolactone triol; castor oil, hydroxyl sunflower oil (HSO) and mixtures thereof.

Castor oil is particularly suitable. Castor oil (*Ricinus* oil) is a pale yellow and viscous liquid, derived from the bean of the castor plant (*Ricinus communis*). Castor oil is predominately made up of triglycerides of fatty acids that contain 87-90% of ricinoleic acid (cis-12-hydroxyoctadec-9-enoic acid), and can be achieved in high purity grades. Castor oil and its derivatives have been used as polyols for polyurethanes and adhesives. The castor oil can be partially hydrogenated. It has been found that castor oil provides the length of the branches and the position of the hydroxyl groups which is particularly suited for providing a chemically cross-linked gel having a pore size which results in slow release of the hydrophobic material, particularly where the hydrophobic material is a perfume. In addition, the chemically cross-linked gels derived from castor oil show less syneresis of the hydrophobic material from the gel.

Polyglycerols are hydroxy-containing ethers. Polyglycerols are typically obtained by the polymerisation of alkylene oxides (such as epoxides). Suitable alkylene oxides include ethylene oxide, propylene oxide, butylene oxide, and mixtures thereof, using chain initiators such as ethylene glycol, propylene glycol, diethyelene glycol, dipropylene glycol, 1,4-butanediol, neopentyl glycol, pentaerythritol, hexanetriol, sorbitol, glycerol, and mixtures thereof. Suitable polyglycerols can be selected from the group consisting of: α,α-diglycerol, α,β-diglycerol, hyperbranched polyglycerol, dendritic polyglycerol, and mixtures thereof. Hyperbranched polyglycerols are aliphatic polyethers with multiple hydroxyl end groups that are obtained from the nonsymmetric polyaddition of glycidol to glycerol resulting in a globular branch-on-branch structure which provides special internal flexibility. Dendritic polyglycerols are a hyperbranched polyglycerol with a well-defined symmetric and spherical three-dimensional structure around a core. Apart from improving gel elasticity, the dendritic structure with sterically shielded core together with the exceptionally high number of functional groups of hyperbranched polyglycerols produces flexible gels with relatively low pore size, which increase the longevity of final composition by reducing the diffusion rate not only as a consequence of physically entrapping the hydrophobic material, but also enhancing H-bonding and Van der Waals interactions. Such polyglycerols can be purchased from Nanopartica GmbH (Germany) and Sigma-Aldrich.

Suitable polyglycerols include: polyethylene glycol, polypropylene glycol, poly(diethylene glycol), poly(dipropylene glycol), poly(1,4-butanediol), poly(neopentyl glycol), poly(1,6-hexanediol), and mixtures thereof. The polyglycerol preferably has from 2 to 50, preferably from 4 to 30 repeat units.

Any suitable cross-linking agent can be used, though cross-linking agents selected from the group consisting of: isocyanates, isothiocynates and mixtures thereof, are preferred. The cross-linking agent can be a linear, branched, or cyclic isocyanate, and mixtures thereof. Cyclic isocyanates and mixtures thereof are preferred. Suitable cyclic isocyanates include heterocyclic isocyanates such as 1,3,5-tris(5-isocyanatopentyl)-1,3,5-triazine-2,4,6(1H,3H,5H)-trione.

Suitable cross-linking agents can be selected from the group consisting of: 1, 4-butane diisocyanate (BDI), 1,6 hexamethylene diisocyanate (HMDI), L-Lysine ethyl ester diisocyanate (LDI), 4,4'-Methylenebis(cyclohexyl isocyanate) (H12MDI), Glycolide-ethylene glycol-glycolide isocyanate (Bezwada, LLC), 4,4'-Methylenebis(phenyl isocyanate) (MDI), 2,4'-Methylenebis(phenyl isocyanate) (MDI), 2,2'-Methylenebis(phenyl isocyanate) (MDI), Isophorone diisocyanate (IPDI), 2,4-toluene diisocyanate (2,4-TDI), 2,6-toluene diisocyanate (2,6-TDI), Poly (hexamethylene diisocyanate) (PDI), 1,3-bis(2-isocyanatopropan-2-yl)benzene, Poly (pentamethylene diisocyanate) and mixtures thereof, preferably 1,6 hexamethylene diisocyanate (HMDI), L-Lysine ethyl ester diisocyanate (LDI), Poly (pentamethylene diisocyanate), Poly (hexamethylene diisocyanate) (PDI), 1,3,5-tris(5-isocyanatopentyl)-1,3,5-triazine-2,4,6(1H,3H,5H)-trione, and mixtures thereof. Such cross-linking agents are available from Sigma-Aldrich and from Covestro under trade name of Desmodur® eco N 7300.

The cross-linking agent can have a viscosity below 2.500 mPa·s at 25° C. and an isocyanate equivalent weight of from 15% to 40%, preferably from 18% to 30%. Such cross linking agents are more easily blended with the polyol. As a result, more uniform gels can be achieved.

The gel can be formed using a molar ratio of polyol (or derivative thereof) to cross-linking agent of from 1:0.75 to 1:2, preferably from 1:0.8 to 1:1.6, more preferably from 1:0.8 to 1:1.2. Such ratios of polyol to cross-linking agent typically result in gels having an elastic modulus G' which is of the same order as the viscous modulus G. In addition, ratios of polyol to cross-linking agent typically result in gels having an elastic modulus G' of above 0.1 kPa, preferably above 1 kPa, even more preferably above 2 kPa, and below 100 kPa.

The gel is preferably essentially free, or free of unreacted isocyanates and/or isothiocyanates.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition dispenser comprising a housing, the housing comprising:

a base portion and a top portion that is rotatably and releasably connectable with the base portion about a longitudinal axis, wherein when the base portion and top portion are connected, an interior and exterior of the housing are defined, wherein the base portion comprises a first surface, a second surface opposing the first surface, and a mounting portion disposed on the second surface, and wherein the top portion comprises a first surface comprising an opening for exposing at least a portion of a volatile composition cartridge and a second surface opposing the first surface;

a recessed track; and a guide protrusion engageable with the recessed track, wherein the recessed track comprises a track opening disposed at an open end of the recessed track and a track stop disposed at an opposite end of the recessed track, wherein the recessed track is disposed on either the base portion or the top portion, and wherein when the recessed track is disposed on the base portion then the guide protrusion is disposed on the top portion, and wherein when the recessed track is disposed on the top portion then the guide protrusion is disposed on the base portion, wherein the recessed track further comprises a restriction disposed adjacent to the track stop, wherein the track opening is configured to receive the guide protrusion, and wherein the recessed track further comprises an axially outermost point disposed adjacent to the track stop, wherein when the guide protrusion is positioned at the axially outermost point on the recessed track, the first surface of the base portion is closer to the second surface of the top portion than any other position of the guide protrusion on the recessed track.

2. The volatile composition dispenser of claim 1, wherein the interior of the housing is configured to at least partially contain a volatile composition cartridge comprising a volatile composition.

3. The volatile composition dispenser of claim 1, wherein the base portion further comprises an actuator extending from the first surface.

4. The volatile composition dispenser of claim 1, further comprising a cover that is removably connectable with the top portion.

5. The volatile composition dispenser of claim 1, wherein when the guide protrusion is positioned at the track stop, the first surface of the base portion and the second surface of the top portion are spaced axially farther apart than when the guide protrusion is positioned at the axially outermost point.

6. The volatile composition dispenser of claim 1, wherein the housing comprises a plurality of air flow apertures.

7. The volatile composition dispenser of claim 1, further comprising a volatile composition cartridge.

8. The volatile composition dispenser of claim 1, wherein the interior is configured to receive a volatile composition cartridge comprising a membrane and a rupturable substrate.

9. The volatile composition dispenser of claim 1, wherein the interior is configured to receive a volatile composition cartridge comprising a solid gel article.

10. The volatile composition dispenser of claim 1, wherein the recessed track is disposed on the top portion and the guide protrusion is disposed on the base portion.

11. The volatile composition dispenser of claim 6, wherein the volatile composition dispenser has a first configuration where at least a portion of the plurality of air flow apertures are covered a second configuration where at least a portion of the plurality of air flow apertures are exposed to the exterior.

* * * * *